United States Patent [19]

Bunczk et al.

[11] Patent Number: 4,780,236

[45] Date of Patent: * Oct. 25, 1988

[54] LAVORATORY CLEANSING BLOCK CONTAINING POLYETHYLENE GYCOL DISTEATRATE, GUAR GUM AND SODIUM CHLORIDE

[75] Inventors: Charles J. Bunczk, Norristown; Peter M. Burke, Downingtown; Edward Strauch, Reading, all of Pa.

[73] Assignee: Kiwi Brands, Inc., Douglasville, Pa.

[*] Notice: The portion of the term of this patent subsequent to Feb. 2, 2005 has been disclaimed.

[21] Appl. No.: 106,132

[22] Filed: Oct. 7, 1987

Related U.S. Application Data

[63] Continuation of Ser. No. 876,923, Jun. 20, 1986, Pat. No. 4,722,801.

[51] Int. Cl.⁴ .......................... C11D 3/04; C11D 3/20; C11D 3/22; C11D 17/00

[52] U.S. Cl. .......................... 252/174; 4/227; 4/228; 134/42; 252/89.1; 252/174.17; 252/174.21; 252/174.22; 252/DIG. 16

[58] Field of Search .................. 4/227, 228; 134/42; 252/89.1, 90, 134, 174, 174.17, 174.21, 174.22, 170, 106, DIG. 16

[56] References Cited

U.S. PATENT DOCUMENTS

| | | | |
|---|---|---|---|
| 3,312,626 | 4/1967 | Hooker | 252/548 |
| 3,901,832 | 8/1975 | Dugan | 252/557 |
| 3,953,353 | 4/1976 | Barrett | 252/174 |
| 4,043,931 | 8/1977 | Jeffrey et al. | 252/93 |
| 4,149,986 | 4/1979 | Dickson | 252/108 |
| 4,248,827 | 2/1981 | Kitko | 422/37 |
| 4,269,723 | 5/1981 | Barford | 252/106 |
| 4,278,571 | 7/1981 | Choy | 252/558 |
| 4,280,994 | 7/1981 | Turney | 424/68 |
| 4,308,625 | 1/1982 | Kitko | 4/228 |
| 4,310,434 | 1/1982 | Choy et al. | 242/174.21 |
| 4,396,522 | 8/1983 | Callicott et al. | 252/163 |
| 4,460,490 | 7/1984 | Barford | 252/92 |
| 4,477,363 | 10/1984 | Wong et al. | 252/134 |
| 4,545,917 | 10/1985 | Smith | 252/90 |
| 4,578,207 | 3/1986 | Holdt et al. | 252/134 |
| 4,624,848 | 11/1986 | Lee | 424/22 |
| 4,629,621 | 12/1986 | Snipes | 424/19 |
| 4,668,510 | 5/1987 | Shetty | 424/78 |

FOREIGN PATENT DOCUMENTS

| | | |
|---|---|---|
| 0053055 | 6/1982 | European Pat. Off. . |
| 58-25398 | 2/1983 | Japan . |
| 58-168699 | 10/1983 | Japan . |
| 59-24797 | 2/1984 | Japan . |
| 61-83300 | 4/1986 | Japan . |
| 78055 | 5/1979 | Luxembourg . |
| 486885 | 4/1970 | Switzerland . |
| 2061996 | 5/1981 | United Kingdom . |

*Primary Examiner*—Dennis Albrecht
*Attorney, Agent, or Firm*—Steele, Gould & Fried

[57] ABSTRACT

Solid cake lavoratory cleansing block composition comprising polyethylene glycol distearate having a dissolution time of at least 5.5 hours, and optional ingredients which include a gelling natural gum, fragrances, dyes, solid binders, filler material and mixtures thereof.

5 Claims, No Drawings

LAVORATORY CLEANSING BLOCK CONTAINING POLYETHYLENE GYCOL DISTEATRATE, GUAR GUM AND SODIUM CHLORIDE

This is a continuation of application Ser. No. 876,923, filed June 20, 1986, now U.S. Pat. No. 4,722,801.

FIELD OF THE INVENTION

The present invention relates to cake compositions whch are useful for the treatment of the flush water of toilets. More particularly, the invention is concerned with a long lasting toilet tank dispenser which may be formed by casting and is responsive to the flushing of the toilet.

BACKGROUND OF THE INVENTION

In treating toilet flush water with chemicals in order to produce desirable effects such as bowl aesthetics, cleaning, disinfection, deodorization, aerosol reduction, etc., it is desirable that the chemicals be dispensed into the flush water automatically each time the toilet is flushed. The prior art discloses numerous devices which have been designed for this purpose. Particularly desirable devices are those comprising a solid cake composition. In this type of device a measured amount of water enters the device during one flush cycle and remains in contact with the cake between flushes, thereby forming a concentrated solution of the composition which is dispensed into the flush water during the next flush. The advantages of such devices are that the chemical composition can be packaged and shipped in more concentrated form than aqueous solutions of the chemicals. Also, the problems of liquid spillage resulting from breakage of the dispensers during shipment or handling is eliminated.

Prior art surfactant cake compositions are disclosed in U.S. Pat. No. 4,308,625, Kitko, issued Jan. 5, 1982 and U.S. Pat. No. 4,043,931, Jeffrey et al, issued Aug. 23, 1977. These patents disclose a lavoratory cleansing tablet which is formed with two or more nonionic surfactants which includes the use of polyalkoxylated alcohols. U.S. Pat. No. 4,477,363, Wong et al, issued Oct. 16, 1984, discloses a solid cake comprising free fatty alcohol and a buffered alkali earth metal alkyl sulfate surfactant. U.S. Pat. No. 4,310,434, Choy et al, issued Jan. 12, 1982; and U.S. Pat. No. 4,278,571, Choy, issued July 14, 1981, entitled "Surfactant Cake Compositions"; all of which are incorporated herein by reference, disclose surfactant cake compositions containing dyes and perfumes which are utilized in the present invention. The surfactants provide cleaning and sudsing in the toilet bowl and also serve to dispense other components of the compositions such as dyes, perfumes, organic resins, etc.

Water-soluble inert salts such as alkali metal chlorides and sulfates are used in such compositions to act as a "filler" so that the composition can be formed into cakes of desirable size without using excessive amounts of active ingredients. The predominant ingredients of the cake compositions are usually the surfactant, perfume and the filler salt.

A major problem in this art has been short and/or erratic longevity of surfactant cakes because of rapid and uneven dissolution resulting in decreased cake stability and longevity.

It has been found that a solid cake composition which is preferably cast and has a long and uniform block life can be provided where the composition comprises the combination of a polyethylene glycol distearate having a specific water solubility and molecular weight range with the conventional materials such as fillers, binders, dyes, fragrances, extenders and the like.

It is an object of the present invention to provide a solid cake compositions which may be formed by casting and comprises a specific kind of polyethylene glycol distearate, which compositions are suitable for use for automatically dispensing cleaning agents into the toilet.

It is a further object of the present invention to provide a cast solid cake composition having relatively high melt temperatures and less block surface tackiness for improved processing.

It is a still further object of the present invention to provide a lavoratory block which has a long and uniform block life that eliminates sluggish toilets.

It is a yet still further object of the present invention to provide a lavoratory block which resists mounding and major fragmentation.

Other objects, advantages and novel features of the present invention will be apparent to those skilled in the art from the following description and appended claims.

SUMMARY OF THE INVENTION

The objectives of the invention are achieved by providing a solid unsupported cake composition which comprises a polyethylene glycol distearate having a drop dissolution time of at least 5.5 hours according to the Distearate Dissolution Test (see Example I hereinafter) and a molecular weight from about 3,000 to 12,000, perferably about 7,000 to 9,000, and optional ingredients selected from the groups consisting of fragrances, dyes, binders, filler material and mixtures thereof. Advantageously, the cake composition comprises from about 8% to about 35% by weight of said polyethylene glycol distearate, perferably, about 12% to 29%. It is known that polyethylene glycol distearate is extremely hydrophilic. Because of the extreme hydrophilic nature of the compound, it would be expected that the material would be very water soluble without any prolonged transition from solid to a liquid. It has been surprisingly found that the particular kind of polyethylene glycol distearate of the invention goes through a hydration stage forming a tenacious gel so as to provide the aforementioned extended block life relative to other formulations containing polyethylene glycol distearate of varying molecular weights.

Another embodiment of the present invention is directed to a long life cake lavoratory cleaning composition which is preferably cast and comprises from about 8% to about 35% by weight, preferably about 12% to 29% of said polyethylene glycol distearate and a natural gum in an amount of from about 3% to about 35% by weight of composition, and conventional materials, such as fillers, dyes, binders, fragrances, and the like. Preferably the gum is guar gum.

It is critical in the present invention that the polyethylene glycol distearate which is utilized in the formulation of the cake composition have a drop dissolution time of at least about 5.5 hours according to the Distearate Dissolution Test. It has been found that not all polyethylene glycol distearates having a molecular weight of about 3,000 to 12,000 posses such a characteristic. Their method of preparation appears to influence their solubility. Perferably, their preparation is according to the method of condensing a fatty acid with an alcohol as described by W. B. Satkowski et al in "Polyoxyethylene esters of Fatty Acids", *Nonionic Surfactants*, M. J. Schick Ed. (Dekker, NY 1967) p. 142-174, which is herein incorporated by reference. For example, stearic acid having a molecular weight of 284.5 is reacted with a polyethylene glycol having a molecular weight range between 5500-8500 to form a polyethylene glycol distearate having a molecular weight range of about 6033-9033. Such compound having a dissolution time of at least 5.5 hours is suitable for use in the invention.

DISCLOSURE OF THE INVENTION

According to the present invention, it has been found that by utilizing polyethylene glycol distearate having a molecular weight from about 3,000 to 12,000 and a dissolution time of at least about 5.5 hours according to the Distearate Dissolution Test, a long life solid cake composition can be obtained.

The compositions of the present invention are in the form of solid cake compositions which comprises:

(A) from about 8% to about 35% by weight, preferably, about 12% to about 29% by weight of a polyethylene glycol distearate having a molecular weight from about 3,000 to 12,000, preferably, about 7,000 to about 9,000 and dissolution time of at least about 5.5 hours according to the Distearate Dissolution Test, and (B) conventional materials such as fillers, dyes, binders, disinfectants, fragrances, and the like.

In order to improve the cake characteristics it has been found advantageous to utilize in the cake composition a greater portion of polyethylene glycol distearate which has a molecular weight between about 7,000 to about 12,000. A greater portion of polyethylene glycol distearate having a molecular weight between about 3,000 to about 7,000, preferably about 3,000 to about 4,000 in combination with the higher molecular weight polyethylene glycol distearate aids in preventing mounding and further acts as a binder.

It has been further found that natural gums can advantageously be utilized as binders in the present invention. The natural gums which may be utilized are those which are cold water gelling additives and develop a high viscosity and a high gel strength. Included in the gums which may be utilized are guar, xanthan, tragacanth, carrageenan, karaya, algin, and the like. The most preferable is guar which has been found to be the most effective in retarding block dissolution and to reduce the problem of sluggish toilet behavior.

It has been found to be particularly advantageous to utilize guar gum together with sodium chloride as a filler since there is a synergistic viscosity increase of water that is not found with other fillers such as calcium sulfate. Additionally, there is an increase of the relative insolubility properties of the matrix in water.

As a further binding agent the use of solid emollients have been found to be helpful to prevent the cake of the invention from mounding out. Suitable emollients include glyceryl monostearate, glyceryl monopalmitate, ethylene glycol stearate, propylene glycol monostearate, and the like, most preferably is glyceryl monostearate which provides a matrix to prevent mounding. The emollients may be utilized in amounts of about 0 to about 10% by weight, preferably about 5% to about 10%.

It has been found to be advantageous to utilize certain nonionic surfactants in the cake formulation. Nonionic surfactants that may be included are the condensation products of a long chain ethylene oxide moiety with an aliphatic alcohol preferably a primary or secondary aliphatic alcohol or alkyl phenol, preferably the primary or secondary alcohol contains 8 to 20 carbon atoms and the alkyl phenol-based moiety is one wherein the alkyl chain is straight or branched and contains 6 to 12 carbon atoms, preferably 6 to 9 carbon atoms.

Illustrative nonionic surfactants having the desired characteristics for formulation are available on the market under the tradename of "Neodol" products by Shell Oil Company; "Tergitol" products by Union Carbide Company; and "Alfol" products by Continential Oil Company. Specific examples include "Neodol 25-7" (linear $C_{12}-C_{15}$ primary alcohol condensed with 7 moles of ethylene oxide per mole of alcohol); "Neodol 45-7" (linear $C_{14}-C_{15}$ primary alcohol mixture condensed with 7 moles of ethylene oxide per mole of alcohol); "Tergitol 15-S7" (random secondary $C_{11}-C_{15}$ alcohol condensed with 7 moles of ethylene oxide per mole of alcohol); and "Alfol 1416-6.5" (primary $C_{14}-C_{16}$ alcohol condensed with 6.5 moles of ethylene oxide per mole of alcohol).

Such nonionic surfactants act as coupling agents to provide an integration of the cake components and may be used in the amount of about 0 to 30% by weight of the cake formulation.

Also useful to enhance the life of the cake are ethoxylated nonylphenols. The high ethoxylated nonylphenol, that is, those having over 20 moles of ethylene oxide per mole of phenol, provides slow dissolution of the cake formulation. Up to about 10% by weight of high ethoxylated nonylphenols is preferably utilized together with the ethoxylated aliphatic alcohols.

Water-soluble inert salts are used in the present compositions as "fillers" so that the composition can be formed into cakes of desired size without using excessive amounts of active ingredients. They are used alone or in combination in amounts up to about 64% by weight.

The inert salts (filler salts) used in the compositions of the present invention can be any water-soluble inorganic or organic salt or mixtures of such salts. For purposes of the present invention, "water-soluble" means having a solubility in water of at least 2.0 grams per hundred grams of water at 20° C. Examples of suitable salts include various alkali metal and/or alkaline earth metal sulfates, chlorides, borates, bromides, citrates, acetates, lactates, etc.

Specific examples of suitable salts include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride. The preferred salts are the inorganic salts, especially the alkali metal sulfates and chlorides. Particularly preferred salts, because of their low cost, are calcium sulfate and sodium chloride. The salts are present in the compositions herein at levels of from about 20% to about 64% by weight (preferably from about 25% to about 35%). Most preferably, sodium chloride is utilized together with guar gum either alone or with other salts since the combination not only provides a synergistic viscosity increase of water and decreases the relative solubility properties of the matrix in water but also aids to prevent mounding.

Calcium sulfate is advantageously utilized alone or together with the other gums or together with sodium chloride because it has a low solubility level which is constant over the water temperature range likely to exist within toilet tanks.

Various optional materials may be included in the compositions herein.

Dyes may be included at levels of from about 2.5% to 15.0% by weight. Examples of suitable dyes are Alizarine Light Blue B (C.I. 63010), Carta Blue VP (C.I. 24401), Acid Green 2G (C.I. 42085), Astragon Green D (C.I. 42040), Supranol Cyanine 7B (C.I. 42675), Maxilon Blue 3RL (C.I. Basic Blue 80), Drimarine Blue Z-RL (C.I. Reactive Blue 18), Alizarine Light Blue H-RL (C.I. Acid Blue 182), FD&C Blue No. 1, FD&C Green No. 3 and Acid Blue No. 9. Others are disclosed in the aforementioned U.S. Pat. Nos. 4,310,434 and 4,477,363, which are herewith incorporated by reference.

The cakes of the invention may also contain up to about 15% by weight of a cationic quaternary ammonium salt.

It is known that the cationic quaternary ammonium salts which include a greater number of short-chain alkyl groups in the structure, incline toward better bacteriostatic properties. Specific examples of bacteriostatic agents that may be used in the compositions of this invention include di-isobutyl cresoxy ethoxy ethyl dimethyl benzyl ammonium chloride, di-isobutyl phenoxy ethoxy ethyl dimethyl benzyl ammonium chloride, myristyl dimethylbenzene ammonium chloride, benzalkonium chloride, cetyl pyridinium chloride, coconut dimethyl benzyl ammonium chloride, stearyl dimethyl benzyl ammonium chloride, alkyl dimethyl benzyl ammonium chloride, alkyl diethyl benzyl ammonium chloride, alkyl dimethyl benzyl ammonium bromide, di-isobutyl phenoxy ethoxy ethyl trimethyl ammonium chloride, di-isobutyl phenoxy ethoxy ethyl dimethyl alkyl ammonium chloride, methyl-dodecylbenzyl trimethyl ammonium chloride, cetyl trimethyl ammonium bromide, octadecyl dimethyl ethyl ammonium bromide, cetyl dimethyl ethyl ammonium bromide, octadecenyl-9-dimethyl ethyl ammonium bromide, dioctyl dimethyl ammonium chloride, dodecyl trimethyl ammonium chloride, octadecyl trimethyl ammonium chloride, octadecyl trimethyl ammonium bromide, hexadecynyl trimethyl ammonium iodide, octyltrimethyl ammonium fluoride, and mixtures thereof. Other water dispersible salts, such as the acetates, sulfates, nitrates, and phosphates, are effective in place of the halides, but the chlorides and bromides are preferred.

The cakes may also contain perfumes to impart an acceptable odor to the flushing water. The perfume may be in solid form and is suitably present in an amount up to 15% by weight. In this connection, it may be noted that the term "perfume" is intended to refer to any material giving an acceptable odor and thus materials giving a "disinfectant" odor such as essential oils, pine extracts, terpinolenes, ortho phenyl phenol or paradichlorobenzene may be employed. The essential oils and pine extracts also contribute as plasticizers and are functional to a degree in extending block life.

Certain perfume materials may be added which additionally function to control the solubility of anionic sulfate surfactants. Examples of such perfume materials are isobornyl acetate, myrtenyl acetate and frenchyl acetate. Other suitable perfumes or fragrances are disclosed in U.S. Pat. No. 4,396,522 of Callicott et al, which is herein incorporated by reference.

The cake formulation may also contain other binding and/or plasticizing ingredients serving to assist in the manufacture thereof, for example, polypropylene glycol having a molecular weight from about 300 to about 10,000 in an amount up to about 20% by weight, preferably about 4% to about 15% by weight of the mixture may be used. The polypropylene glycol reduces the melt viscosity, acts as a demolding agent and also acts to plasticize the block when the composition is prepared by a casting process. Other suitable plasticizers such as pine oil fractions, d-limonene, dipentene and the ethylene oxide-propylene oxide block copolymers may be utilized.

The blocks of the present invention can be produced by a variety of process, e.g., casting/moulding process, by tablet compression process or by an extrusion process. The casting process is the preferred process of the invention.

The casting process which is well within the skill of those in the art involves the melting of the ingredients and then casting the melt into appropriate shaped moulds and allowing the melt to cool and solidify. The shaped tablets or blocks each suitably having a weight of from 20 to 150 grams, preferably from 30 to 70 grams.

The shaped tablets or blocks of the preferred embodiments of the invention comprise:

from about 8% to about 35% by weight of polyethylene glycol distearate having a molecular weight of 3,000–12,000 and a dissolution time of at least 5.5 hours according to the Distearate Dissolution Test;

up to about 10% by weight of glyceryl monostearate;

up to about 30% by weight of an ethoxylated $C_8$–$C_{20}$ aliphatic alcohol;

up to about 10% by weight of ethoxylated nonylphenol;

from about 4% to about 15% by weight of plasticizer;

up to about 35% by weight of guar gum;

up to about 32% by weight of sodium chloride;

up to about 32% by weight of calcium sulfate, and up to about 15% of disinfecting agents, coloring and/or fragrances.

In order tha the invention may be better understood the following examples are given by way of illustration only. In the examples, all parts and percentages are by weight unless otherwise stated.

The following examples are for compositions suited for forming shaped bodies of blocks by a casting/moulding operation.

EXAMPLE I

Distearate Dissolution Test

To determine the dissolution rate of polyethylene glycol distearate in water the test is performed as follows:

A sample of the polyethylene glycol distearate is placed into a beaker and heated so as to form a melt. Using a 7.5 ml capacity polyethylene transfer pipet, one drop of the melt is place in the center of a petri dish. The drop is allowed to fully solidify for ten minutes, then 75 ml of deionized water is added to the dish. The dish is monitored to determine the time required for the drop of surfactant to totally dissolve.

A dissolution time of at least about 5.5 hours indicates that the polyethylene glycol distearate with the desired molecular weight is suitable for use in formulating the composition of the invention.

EXAMPLE II

A. Procedure for the Selection of Polyethylene Glycol 6000 Distearate (PEG 6000DS)

To determine the dissolution rate of polyethylene glycol distearate in water the test is performed as follows:

1. An aliquot of PEG 6000DS is placed in a beaker and melted.
2. Using a 7.5 ml polyethylene transfer pipet, a drop of the melt is transferred to a microscope glass slide, the weight of PEG 6000DS added being 0.02+ or −0.001 g using an analytical balance. The melt is allowed to solidify for ten minutes.
3. The glass slide is carefully placed in a 1000 ml glass beaker containing 800 cc deionized water which is immersed in a 38° C. water bath.
4. The beaker is monitored to determine the time necessary for the drop of PEG 6000DS to totally dissolve. A dissolution time of at least 5.5 hours indicated that the polyethylene glycol distearate was suitable for use in formulating the composition of the invention.

B. Preparation of Cake Composition

| | |
|---|---|
| Polyethylene glycol 6000 distearate from part A | 21.0% |
| Ethoxylated $C_{12}$–$C_{15}$ Linear, Primary Alcohol with 7 EO | 29.5% |
| Ethoxylated Nonylphenol with 100 EO | 5.5% |
| Ethylene oxide-propylene oxide block copolymer (8500 molec. wt., 80% EO) | 3.5% |
| Acid Blue #9 dye | 5.5% |
| Dipentene | 8.0% |
| Ortho-phenyl phenol | 1.0% |
| Guar gum | 5.5% |
| Sodium chloride | 20.5% |

Into a first mixture vessel four-fifths of the ethoxylated $C_{12}$–$C_{15}$ linear primary alcohol is added and slowly heated with stirring. The polyethylene glycol 6000 distearate, ethoxylated nonylphenol and ethylene oxide-propylene oxide block copolymer are added and the mixture is heated with stirring to 71° C. to form a clear melt.

In a separate vessel the remaining one-fifth of the ethoxylated linear primary alcohol there is added with stirring the dye, the dipentene and the ortho-phenyl phenol. The mixture is then added to the first mixing vessel followed by the guar gum and the sodium chloride. The mixture is cooled to 57° C. and poured into molds. After cooling to 5° C., the blocks are removed from the mold.

EXAMPLE III

Following the procedure of Example II, a shaped lavoratory cake composition is prepared with the following ingredients:

| | |
|---|---|
| Polyethylene glycol 6000 distearate | 9.0% |
| Glyceryl monostearate | 5.5% |
| Ethoxylated $C_{12}$–$C_{15}$ Linear, Primary Alcohol with 7 EO | 20.0% |
| Ethoxylated Ceto Stearyl Alcohol with 50 EO | 17.5% |
| Acid Blue #9 dye | 5.5% |
| Terpinolene | 8.0% |
| Ortho-phenyl phenol | 1.0% |
| Guar gum | 9.5% |
| Sodium chloride | 24.0% |

EXAMPLE IV

Following the procedure of Example II, a shaped cake composition is prepared with the following ingredients:

| | |
|---|---|
| Polyethylene glycol (6000) distearate | 20.0% |
| Glyceryl monostearate - acid stable | 10.0% |
| Ethoxylated aliphatic alcohol (Neodol 45-7) | 20.0% |
| Guar gum | 9.0% |
| Sodium chloride | 26.0% |
| Polypropylene glycol (PPGD1000) | 5.0% |
| Cetyl trimethyl ammonium bromide | 1.0% |
| Acid blue dye no. 9 | 4.0% |
| Terpinolene | 5.0% |

The composition had a melt viscosity of 2000 cps at 49° C. and a set point at 46° C. The shaped tablet had an in-tank life of more than 30 days and showed only slight mounding.

EXAMPLE V

Following the procedure of Example II, a shaped cake composition is prepared with the following ingredients:

| | |
|---|---|
| Polyethylene glycol (6000) distearate | 20.0% |
| Glyceryl monostearate - acid stable | 10.0% |
| Ethoxylated aliphatic alcohol (Neodol 45-7) | 21.0% |
| Guar gum | 6.0% |
| Sodium chloride | 26.0% |
| Polypropylene glycol (PPGD1000) | 6.0% |
| Cetyl trimethyl ammonium bromide | 1.0% |
| Acid blue dye no. 9 | 4.0% |
| Terpinolene | 6.0% |

The composition had a melt viscosity of 1120 cps at 51° C. and a set point at 46° C. The shaped tablet had an in-tank life of 20–40 days in 6 different toilets and mounded out after 30 days.

EXAMPLE VI

Following the procedure of Example II, a shaped cake composition is prepared with the following ingredients:

| | |
|---|---|
| Polyethylene glycol (6000) distearate | 16.5% |
| Glyceryl monostearate - acid stable | 5.5% |
| Ethoxylated aliphatic alcohol (Neodol 45-7) | 25.0% |
| Guar gum | 6.0% |
| Sodium chloride | 32.0% |
| Polypropylene glycol (PPGD1000) | 5.0% |
| Cetyl trimethyl ammonium bromide | 1.0% |
| Acid blue dye no. 9 | 4.0% |
| Terpinolene | 5.0% |

The shaped composition had an in-tank life of about 30 days and showed only slight flattening.

EXAMPLE VII

Following the procedure of Example II, a shaped cake composition is prepared with the following ingredients:

| | |
|---|---|
| Polyethylene glycol (6000) distearate | 12.5% |
| Glyceryl monostearate - acid stable | 5.5% |
| Ethoxylated aliphatic alcohol (Neodol 45-7) | 23.0% |
| Ethoxylated nonylphenol (NP100) | 4.0% |
| Guar gum | 8.0% |
| Sodium chloride | 32.0% |
| Polypropylene glycol (PPGD1000) | 5.0% |
| Cetyl trimethyl ammonium bromide | 1.0% |
| Acid blue dye no. 9 | 4.0% |
| Terpinolene | 5.0% |

The shaped composition had an in-tank life of about 25-30 days in 6 different toilets and showed only slight mounding.

EXAMPLE VIII

Following the procedure of Example II, a shaped cake composition is prepared with the following ingredients:

| | |
|---|---|
| Polyethylene glycol (6000) distearate | 16.5% |
| Glyceryl monostearate | 5.5% |
| Ethoxylated aliphatic alcohol (Neodol 45-7) | 23.0% |
| Calcium sulfate | 32.0% |
| Guar gum | 8.0% |
| Polypropylene glycol (PPGD1000) | 5.0% |
| Cetyl trimethyl ammonium bromide | 1.0% |
| Acid blue dye no. 9 | 4.0% |
| Terpinolene | 5.0% |

The shaped tablet mounded out after 30 days in-tank. In lieu of guar gum, an equal amount of any one of the aforementioned natural gums may be utilized.

EXAMPLE IX

Following the procedure of Example II, a shaped cake composition is prepared with the following ingredients:

| | |
|---|---|
| Polyethylene glycol (6000) distearate | 30.0% |
| Glyceryl monostearate | 20.0% |
| Ethoxylated ceto stearyl alcohol with 50 EO | 20.0% |
| Acid blue dye no. 9 | 4.0% |
| Cetyl trimethyl ammonium bromide | 1.0% |
| Calcium sulfate | 25.0% |

The resulting block had the following characteristics:

| | |
|---|---|
| Demolding | Drop Out |
| Block surface | Dry |
| Specific gravity | 1.11 |

EXAMPLE X

Following the procedure of Example II, a shaped cake composition is prepared with the following ingredients:

| | |
|---|---|
| Polyethylene glycol (6000) distearate | 20.0% |
| Glyceryl monostearate | 15.0% |
| Ethoxylated ceto stearyl alcohol with 50 EO | 20.0% |
| Ethoxylated aliphatic alcohol (Neodol 25-7) | 5.0% |
| Acid blue dye no. 9 | 4.0% |
| Cetyl trimethyl ammonium bromide | .9% |
| Polypropylene glycol 425 | 10.0% |
| Calcium sulfate | 20.1% |
| Terpinolene | 5.0% |

The resulting block had the following characteristics:

| | |
|---|---|
| Demolding | Light Tap |
| Block surface | Dry |
| In-tank life (days) | 30 |
| Mounding | slight mounding |

EXAMPLE XI

Following the procedure of Example II, a shaped cake composition is prepared with the following ingredients:

| | |
|---|---|
| Polyethylene glycol (6000) distearate | 20.0% |
| Glyceryl monostearate | 10.0% |
| Ethoxylated ceto stearyl alcohol with 50 EO | 20.0% |
| Ethoxylated aliphatic alcohol (Neodol 25-7) | 5.0% |
| Acid blue dye no. 9 | 4.0% |
| Cetyl trimethyl ammonium bromide | .9% |
| Polypropylene glycol 425 | 10.0% |
| Calcium sulfate | 25.1% |
| Terpinolene | 5.0% |

The resulting block had the following characteristics:

| | |
|---|---|
| Demolding | Drop Out |
| Block surface | Dry |
| Specific gravity | 1.19 |
| Mounding | slight mounding |

EXAMPLE XII

Following the procedure of Example II, a shaped cake composition is prepared with the following ingredients:

| | |
|---|---|
| Polyethylene glycol (6000) distearate | 20.0% |
| Glyceryl monostearate | 12.0% |
| Ethoxylated ceto stearyl alcohol with 50 EO | 20.0% |
| Ethoxylated aliphatic alcohol (Neodol 25-7) | 6.0% |
| Acid blue dye no. 9 | 4.0% |
| Cetyl trimethyl ammonium bromide | .9% |
| Polypropylene glycol 425 | 9.0% |
| Calcium sulfate | 23.1% |
| Terpinolene | 5.0% |

The resulting block had the following characteristics:

| | |
|---|---|
| Demolding | Drop Out |
| Block surface | Dry |
| Specific gravity | 1.21 |
| In-tank life (days) | 27 |
| Mounding | none |

EXAMPLE XIII

Following the procedure of Example II, a shaped cake composition is prepared with the following ingredients:

| | | |
|---|---|---|
| Polyethylene glycol (6000) distearate | 22.5% | |
| Glyceryl monostearate | 10.0% | |
| Ethoxylated ceto stearyl alcohol with 50 EO | 17.5% | |
| Ethoxylated aliphatic alcohol (Neodol 25-7) | 5.0% | |
| Acid blue dye no. 9 | 4.0% | |
| Cetyl trimethyl ammonium bromide | .5% | |
| Polypropylene glycol 425 | 10.0% | |
| Calcium sulfate | 25.5% | |
| Terpinolene | 5.0% | |

The resulting block had the following characteristics:

| | |
|---|---|
| Demolding | Light Tap |
| Block surface | Dry |
| Specific gravity | 1.24 |
| In-tank life (days) | 8 toilets, 20–26 days |
| Mounding | none |

EXAMPLE XIV

Procedure for Preliminary Evaluation of the Mounding and Coupling Properties of a Toilet Block To determine the potential for a block to (1) mound or spread out from its original shape; and (2) remain an intergrated unit once the block has been immersed in water, a test is conducted as follows:

1. Two 2000 ml glass beakers are filled with tap water. One is placed in a refrigerator at about 5° C. for at least four hours while the other beaker remains at ambient temperature.

2. One block from the sample lot is placed in each beaker. The blocks remain immersed in water overnight or about sixteen hours.

3. The blocks are then observed after the immersion period. The ambient temperature sample provides an indication of the degree of spreading or enlarging of the block base that may occur during immersion within a toilet tank. The 5° C. sample provides an indication of the integration of the block components or tendency to dissolve in unison.

The principals, preferred embodiments and modes of operation of the present invention have been described in the foregoing specification. The invention which is intended to be protected herein, however, is not to be construed as limited to particular forms disclosed, since these are to be regarded as illustrative rather than restrictive. Variations and changes may be made by those skilled in the art without departing from the spirit of the invention.

What is claimed is:

1. A solid cake lavoratory cleansing block composition comprising from about 8% to about 35% by weight of composition of polyethylene glycol distearate having a molecular weight from about 3,000 to about 12,000 and a dissolution time of at least about 5.5 hours according to the Distearate Dissolution Test, 3 to about 35% by weight of composition of guar gum, sodium chloride in an amount sufficient for providing a synergistic viscosity increase in water and the relative insolubility of the total block, and the remainder being optional ingredients selected from the following fragrances, dyes, binders, filler material and mixtures thereof.

2. The cleansing block composition of claim 1 including an amount of up to about 10% by weight of composition of a binding agent which is selected from the group consisting of glyceryl monostearate, glyceryl monopalmitate, ethylene glycol stearate, and propylene glycol monostearate.

3. The cleansing block composition of claim 1 including an amount of up to 10% by weight of composition of ethoxylated nonylphenol.

4. The cleansing block composition of claim 1 including a plasticizer selected from the group consisting of polypropylene glycol, dipentene, pine oil fractions, d-limonene and ethylene oxide-propylene oxide copolymers.

5. The cleansing block composition of claim 1 wherein said polyethylene glycol distearate comprises a mixture of polyethylene glycol distearate having a molecular weight between about 7,000 to about 12,000 and polyethylene glycol distearate having a molecular weight between about 3,000 to about 7,000, said polyethylene glycol distearate having a molecular weight between about 7,000 to about 12,000 being present in said formulation in an amount greater than polyethylene glycol distearate having a molecular weight between about 3,000 to about 7,000.

* * * * *